(12) United States Patent
Lucchesi

(10) Patent No.: US 8,642,817 B1
(45) Date of Patent: Feb. 4, 2014

(54) METHOD OF CONVERTING METHANE TO METHANOL

(71) Applicant: Peter J. Lucchesi, Princeton, NJ (US)

(72) Inventor: Peter J. Lucchesi, Princeton, NJ (US)

( * ) Notice: Subject to any disclaimer, the term of this patent is extended or adjusted under 35 U.S.C. 154(b) by 0 days.

(21) Appl. No.: 13/734,040

(22) Filed: Jan. 4, 2013

Related U.S. Application Data

(60) Provisional application No. 61/698,923, filed on Sep. 10, 2012.

(51) Int. Cl.
*C07C 29/09* (2006.01)
*C07C 29/58* (2006.01)

(52) U.S. Cl.
USPC .......................................... 568/893; 568/91

(58) Field of Classification Search
USPC ................................ 568/893, 891
See application file for complete search history.

(56) References Cited

U.S. PATENT DOCUMENTS

| | | |
|---|---|---|
| 5,720,858 A | 2/1998 | Noceti et al. |
| 6,137,017 A | 10/2000 | Stauffer |
| 6,156,211 A | 12/2000 | Gonzalez-Martin et al. |
| 8,173,851 B2 | 5/2012 | Waycuilis et al. |
| 8,211,825 B2 | 7/2012 | Mei et al. |

*Primary Examiner* — Elvis O Price
(74) *Attorney, Agent, or Firm* — Chainey P. Singleton; Edwin S. Flores; Chalker Flores, LLP

(57) ABSTRACT

The present invention includes a method for converting methane to methanol by providing a methane source to provide methane; contacting the methane with chlorine; exposing the methane to a light source to form methyl chloride; converting the methyl chloride with H20 to methanol and hydrochloric acid; converting the hydrochloric acid to chlorine; and purifying the methanol.
The chemical cycle can be applied to the synthesis of alkane alcohols higher than methanol where appropriate.

21 Claims, No Drawings

METHOD OF CONVERTING METHANE TO METHANOL

CROSS-REFERENCE TO RELATED APPLICATIONS

This patent application is a non-provisional patent application of U.S. provisional patent application 61/698,923 filed on Sep. 10, 2012 and entitled "Method of Converting Methane to Methanol" the content of each of which is hereby incorporated by reference in its entirety.

STATEMENT OF FEDERALLY FUNDED RESEARCH

None.

INCORPORATION-BY-REFERENCE OF MATERIALS FILED ON COMPACT DISC

None.

TECHNICAL FIELD OF THE INVENTION

The present invention relates generally to compositions and methods for the synthesis of methanol and in particular, to compositions and methods for the synthesis of methanol involving a cycle which includes the photocatalytic conversion of methane.

The present invention relates to an improvement in processes designed to produce methyl alcohol from natural gas using chlorination technology. The improvement permits the use of natural gas containing significant levels of inert gases while achieving high methane efficiencies. The process encompasses the use of multiple thermal chlorination reactors, each with a natural gas recycle loop. These reactors are arranged in a cross-flow reactor system whereby the gas purge from the first thermal reactor is fed to the second, and so on until the last thermal reactor, which is vented to the atmosphere.

BACKGROUND OF THE INVENTION

Without limiting the scope of the invention, its background is described in connection with the photocatalytic conversion of methane to methanol. Methane, a major component of natural gas, is an abundant material world-wide; however, it is difficult and costly to transport as a gas. The conversion of methane to a more easily transported source (e.g., methanol) is important in many industries including the oil and gas industry. In addition, methanol is a key building block to many valuable chemical products. Production of alcohols by oxidation has been difficult because the oxidation reaction tends to completion to carbon dioxide and over-oxidation is a persistent problem. Therefore, conventional approaches to synthesize methanol from methane generally have poor conversion efficiencies, slow reaction rates, and requires abundant energy sources, making them impractical.

For example, U.S. Pat. No. 8,211,825, entitled, "Methanol Oxidation Catalyst," discloses a methanol oxidation catalyst comprising a material of composition: PtxMzTau in which Pt is platinum, Ta is tantalum, M is an element which comprises at least one selected from the group consisting of V (vanadium), W (tungsten), Ni (nickel) and Mo (molybdenum), x is 40 to 98%, z is 1.5 to 55%, and u is 0.5 to 40%. To maximize catalytic activity the material is preferably in the form of nanoparticles. The values of x, z, and u are selected such that the element exhibits X-ray photoelectron spectroscopy peaks derived from an oxygen bond and a metal bond in which a peak area derived from the oxygen bond is twice or less the peak area derived from the metal bond.

For example, U.S. Pat. No. 8,173,851, entitled, "Processes for Converting Gaseous Alkanes to Liquid Hydrocarbons," discloses a process for converting gaseous alkanes to olefins, higher molecular weight hydrocarbons or mixtures thereof wherein a gaseous feed containing alkanes is thermally reacted with a dry bromine vapor to form alkyl bromides and hydrogen bromide. Poly-brominated alkanes present in the alkyl bromides are further reacted with methane over a suitable catalyst to form monobrominated species. The mixture of alkyl bromides and hydrogen bromide is then reacted over a suitable catalyst at a temperature sufficient to form olefins, higher molecular weight hydrocarbons or mixtures thereof and hydrogen bromide. Various methods are disclosed to remove the hydrogen bromide from the higher molecular weight hydrocarbons, to generate bromine from the hydrogen bromide for use in the process, and to selectively form monobrominated alkanes in the bromination step.

For example, U.S. Pat. No. 6,156,211, entitled, "Enhanced Photocatalytic Conversion of Methane to Methanol Using a Porous Semiconductor Membrane," discloses a method and apparatus for the conversion of methane in solution or gas which provides a photochemical conversion in a unique two-phase boundary system formed in each pore of a semiconductor membrane in a photocatalytic reactor. In a three-phase system, gaseous oxidant, methane contained in a liquid, and solid semiconductor photocatalyst having a metal catalyst disposed thereon, meet and engage in an efficient conversion reaction. The porous membrane has pores which have a region wherein the meniscus of the liquid varies from the molecular diameter of water to that of a capillary tube resulting in a diffusion layer that is several orders of magnitude smaller than the closest known reactors.

For example, U.S. Pat. No. 5,720,858, entitled, "Method for the Photocatalytic Conversion of Methane," discloses a method for converting methane to methanol which involves subjecting the methane to visible light in the presence of a catalyst and an electron transfer agent. Another embodiment of the invention provides for a method for reacting methane and water to produce methanol and hydrogen comprising preparing a fluid containing methane, an electron transfer agent and a photolysis catalyst, and subjecting said fluid to visible light for an effective period of time.

For example, U.S. Pat. No. 6,137,017, entitled, "Methanol Process for Natural Gas Conversion," discloses a process for producing methyl alcohol from natural gas using chlorination technology. The process includes reacting methyl chloride, hydrogen chloride, oxygen and perchloroethylene in a catalytic reactor to give methanol product and hexachloroethane and using the $C_2C_{16}$ to chlorinate methane of natural gas feedstock in multiple thermal chlorination reactors, each with a natural gas recycle loop. These reactors are arranged in a cross-flow reactor system whereby a gas purge from the first reactor is fed to the second, and so on if necessary until a last reactor, which is vented to the atmosphere by feeding a purge steam to the catalytic reactor.

SUMMARY OF THE INVENTION

Therefore, there is a need for a process that produces methanol in a gas or liquid form. It would be desirable if the process was cost effective, easy to operate, relatively fast, and capable of achieving high conversion.

The present invention provides a method for converting methane to methanol by providing a methane source, contacting the methane with chlorine, exposing the mixture to a light source to form methyl chloride; converting the methyl chloride to methanol and hydrochloric acid; converting the hydrochloric acid to chlorine; and purifying the methanol. The light source may be selected from visible light, ultraviolet light and mixtures thereof. In one embodiment the light source is an ultraviolet lamp that is positioned to pass through an ultraviolet transmission surface. The light source is an ultraviolet lamp which includes the ultraviolet wavelength range of 300-400 nm. The methane is sourced from natural gas, coal-bed methane, regasified liquefied natural gas, gas derived from gas hydrates and/or chlathrates, gas derived from anaerobic decomposition of organic matter or biomass, gas derived in the processing of tar sands, synthetically produced natural gas or alkanes, or mixtures of these sources. For example, the methane source may be from natural or synthetically produced alkanes, natural or synthetically produced natural gas, it may also be produced from the recently developed technology involving methane in shale formations—so called "fracking" process. In addition the methane may in some cases be pretreated by saturating the methane with water.

The present invention also provides a method for converting a gaseous alkane to an alkane alcohol by providing a gaseous alkane source, contacting the alkane with a halogen; exposing the alkane to a light source to form an alkane halide; converting the alkane halide to an alkane alcohol and a hydrogen halide acid; converting the hydrogen halide acid to a halide; and purifying the alkane alcohol. The light source may be selected from visible light, ultraviolet light and mixtures thereof.

The present invention provides a process of reacting chlorine with methane to form methanol by contacting the methane with chlorine; exposing the methane to a light source to form methyl chloride; converting the methyl chloride to methanol and hydrochloric acid; converting the hydrochloric acid to chlorine; and purifying the methanol.

The present invention also provides a method for converting methane to methanol comprising the steps of subjecting a mixture of methane and water to light in the presence of chlorine to form methyl chloride; and converting the methyl chloride to methanol.

The present invention also provides a method for reacting methane and water to produce methanol and hydrogen by providing a methane source to provide methane; contacting the methane with chlorine; exposing the mixture to a light source to form methyl chloride; converting the methyl chloride to methanol and hydrochloric acid; converting the hydrochloric acid to chlorine; and purifying the methanol.

BRIEF DESCRIPTION OF THE DRAWINGS

None.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "Alkanes" denotes but is not limited to methane, ethane, propane, butane, isobutene, pentanes, hexanes, and/or cyclohexane, etc.

As used herein, the term "The feed stock" denotes but is not limited to natural gas, associated gas, coal-bed methane, residual hydrocarbon fractions, biomass and/or coal, and shales.

The present inventor realized that there is a need for a process that produces methanol in a process that is cost effective, easy to operate, relatively fast, and capable of achieving high conversion. One common source of methane can be natural gas. Although inexpensive and abundant, natural gas presents difficulties in its use caused by the fact that it contains a number of constituents besides methane including nitrogen, ethane, inerts and carbon dioxide.

The present inventor realized that efficient synthesis of methanol from methane has been an elusive target for many years. It is difficult, if not impossible, because of a basic problem based on the chemistry of methane.

Even if one is able to efficiently convert one of the 4 carbon-hydrogen bonds in methane, the conversion will not stop there because the remaining carbon-hydrogen bonds are weakened by the conversion, and the attacking reagent can easily break the remaining carbon-hydrogen bonds. The present invention offers a novel way to synthesize methanol from methane via chlorine chemistry.

(1)

(2)

(3)

(Net)

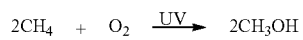

The skilled artisan will recognize the reactions involved.

One aspect of the invention provides a process to convert alkanes into alcohols and more specifically to a process to convert methane into methanol. In a first step, methane is mixed with chlorine and exposed to an ultraviolet light source to form methylchloride and hydrochloric acid. In the second step, methylchloride is mixed with water to form methanol and hydrochloric acid. In a third step, the hydrochloric acid is mixed with oxygen to form water and regenerate the chlorine. The skilled artisan will understand how to prepare these reaction chambers for the reaction, and connect the reagents and products for optimal reactivity.

The process includes halogenating one or more alkanes with one or more halogens to form one or more alkane halides and one or more hydrogen halide acids through the exposure to an ultraviolet light source. The one or more alkane halides are reacted with water to form an alkane alcohol and one or more hydrogen halide acids. The one or more hydrogen halide acids then reacted with oxygen to regenerate one or more halogens and water. The net reaction includes the reaction of one or more alkanes with oxygen with the exposure to an ultraviolet light source to produce an alkane alcohol. It should be noted that the term "one or more" applies for the production of a monohydric alcohol or an alcohol containing more than one hydroxide functionality. The conversion of methane to methyl alcohol is the prime, but not the only desired alcohol-forming reaction. To repeat, to produce mainly methanol, methane is reacted with chlorine to form chloromethane and hydrochloric acid through exposure to a source of ultraviolet light. A specific example includes the conversion of methane to methanol. The process includes halogenating methane with chlorine to form methylchloride and hydrochloric acid through the exposure to an ultraviolet light source. The methylchloride is reacted with water to form methanol and hydrochloric acid. The hydrochloric acid then reacts with oxygen to regenerate chlorine and water. The net reaction is the conversion of methane and oxygen to methanol with the exposure to ultraviolet light.

Generally, alkanes (methane, ethane, propane, butane, isobutene, pentanes, hexanes, and cyclohexane, etc.) react with molecular chlorine to form alkylchlorides. High conversions of methane and very good selectivity to methanol are expected because the cycle is very efficient.

In the operation of the method and apparatus, chlorine is received from a suitable source through a line and is directed to a chlorine storage container. Although this specific example uses chlorine the skilled artisan will readily understand that other halogens may be used to form the "halogenation cycle". Methane from a suitable source is directed to the reactor. Within the reactor the methane and the chlorine are mixed together at an appropriate temperature and exposed to a source of ultraviolet radiation thereby converting the methane and the chlorine to methyl chloride ($CH_3Cl$) and hydrogen chloride (HCl). From the reactor, the $CH_3Cl$, the HCl, and any unreacted methane and by-products $CH_2Cl_2$, $CHCl_3$, and $CCl_4$ are directed to a condenser through a line. The by-products $CH_2Cl_2$, $CHCl_3$, and $CCl_4$ are sent through a line to a converter to react with methane. In the converter, methane reacts with the by-products $CH_2Cl_2$, $CHCl_3$, and $CCl_4$ to form $CH_3Cl$. The newly formed $CH_3Cl$ and unreacted $CH_2Cl_2$, $CHCl_3$, and $CCl_4$ and methane are sent to the condenser. From the condenser methane, HCl, and $CH_3Cl$ are sent to a converter. In the converter HCl and $CH_3Cl$ are converted to $CH_3OH$, and $H_2O$, which are sent to a separator along with unreacted methane and $CH_3Cl$. In the separator, methanol/water are separated as products and recovered. The methanol is subsequently removed from the water. $CH_3Cl$ is sent back to the converter and methane from the separator is sent back to the chlorination reactor. In the converter, the chloride is regenerated, while the chlorine and unreacted oxygen are sent to a condenser, after which they are separated in a separator. The chlorine is sent to the storage container, while the oxygen is sent to the converter through a blower and a line. From the converter, the water, chloromethane, and methane are separated in a separator. Methane is recycled to the converter, chloromethane is sent to the reactor, water is sent to the reactor. In the reactor, chloromethane reacts to form methanol.

It would be possible to feed a stream of methane containing methyl chloride to the hydrolysis reactor, the simplest procedure is to separate methyl chloride from unreacted methane beforehand. The methyl chloride can be scrubbed from the methane by absorption in, for example, a refrigerated stream of perchloroethylene. The separated methane is recycled to the chlorination reactor.

The overall reaction is isothermic and therefore may be driven by fractional recovery of higher chlorides and removal of chloromethane from the reaction mixture, all in the presence of excess methane. In the embodiment, a biomass is gasified in a gasification step to produce methane; however in other embodiments, methane could be provided in the gas phase initially. The present invention may be used for the conversion of hydrocarbonaceous feed stocks into normally liquid and/or normally solid hydrocarbons. The feed stock (e.g. natural gas, associated gas, coal-bed methane residual hydrocarbon fractions, biomass and/or coal) is converted to methanol.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedure described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one", but it is also consistent with the meaning of "one or more", "at least one", and "one or more than one". The use of the term "or" in the claims is used to mean "and/or" unless explicitly indicated to refer to alternatives only or the alternatives are mutually exclusive, although the disclosure supports a definition that refers to only alternatives and "and/or". Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof is intended to include at least one of: A, B, C. AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for converting methane to methanol comprising the steps of:
   providing a methane source to provide methane;
   contacting the methane with chlorine;
   exposing the methane to an ultraviolet light source to form methyl chloride;
   converting the methyl chloride to methanol and hydrochloric acid;
   converting the hydrochloric acid to chlorine; and
   purifying the methanol.

2. The method of claim 1 wherein the ultraviolet light source is an ultraviolet lamp through an ultraviolet transmission surface.

3. The method of claim 1 wherein the ultraviolet which includes the ultraviolet wavelength range of 300-400 nm.

4. The method of claim 1 wherein the methane source are sourced from natural gas, coal-bed methane, regasified liquefied natural gas, gas derived from gas hydrates and/or chlathrates, gas derived from anaerobic decomposition of organic matter or biomass, gas derived in the processing of tar sands, synthetically produced natural gas or alkanes, or mixtures of these sources.

5. The method of claim 1 wherein methane source is from synthetically produced alkanes.

6. The method of claim 1 wherein methane source is from synthetically produced natural gas.

7. The method of claim 1 wherein the methane is pretreated.

8. The method of claim 7 wherein the methane is pretreated by saturating the methane with water.

9. A method for converting a gaseous alkane to an alkane alcohol comprising the steps of:
   providing a gaseous alkane source to provide an alkane;
   contacting the alkane with a halogen;
   exposing the alkane to an ultraviolet light source to form an alkane halide;
   converting the alkane halide to an alkane alcohol and a hydrogen halide acid;
   converting the hydrogen halide acid to a halide; and purifying the alkane alcohol.

10. A process of reacting chlorine with methane to form methanol comprising the steps of:
    providing a methane source to provide methane;
    contacting the methane with chlorine;
    exposing the methane/chlorine mixture to an ultraviolet light source to form methyl chloride;
    converting the methyl chloride to methanol and hydrochloric acid by reaction with water;
    converting the hydrochloric acid to chlorine thereby regenerating the chlorine and purifying the methanol.

11. A method for converting methane to methanol comprising the steps of
    subjecting a mixture of methane and water to an ultraviolet light in the presence of chlorine to form methyl chloride; and converting the methyl chloride to methanol.

12. A method for reacting methane and water to produce methanol and hydrogen comprising the steps of:
    providing a methane source to provide methane;
    contacting the methane with chlorine;
    exposing the methane chlorine mixture to an ultraviolet light source to form methyl chloride;
    converting the methyl chloride to methanol and hydrochloric acid;
    converting the hydrochloric acid to chlorine; and
    purifying the methanol.

13. The method of claim 9 wherein the gaseous alkane is from natural gas, coal-bed methane, regasified liquefied natural gas, gas derived from gas hydrates and/or chlathrates, gas derived from anaerobic decomposition of organic matter or biomass, gas derived in the processing of tar sands, synthetically produced natural gas or alkanes, or mixtures of these sources.

14. The method of claim 9 wherein the gaseous alkane is a synthetic gaseous alkane.

15. The method of claim 9 wherein the gaseous alkane is pretreated.

16. The method of claim 10 wherein the methane source is from natural gas, coal-bed methane, regasified liquefied natural gas, gas derived from gas hydrates and/or chlathrates, gas derived from anaerobic decomposition of organic matter or biomass, gas derived in the processing of tar sands, synthetically produced natural gas or alkanes, or mixtures of these sources.

17. The method of claim 10 wherein methane source is synthetically produced.

18. The method of claim 12 wherein the ultraviolet light source includes the ultraviolet wavelength range of 300-400 nm.

19. The method of claim 12 wherein the methane source is from natural gas, coal-bed methane, regasified liquefied natural gas, gas derived from gas hydrates and/or chlathrates, gas derived from anaerobic decomposition of organic matter or biomass, gas derived in the processing of tar sands, synthetically produced natural gas or alkanes, or mixtures of these sources.

20. The method of claim 12 wherein methane source is synthetically produced.

21. The method of claim 12 wherein the methane is pretreated by saturating the methane with water.

* * * * *